United States Patent [19]

Rahn

[11] 4,269,518
[45] May 26, 1981

[54] STRAY LIGHT ELIMINATOR IN A SCATTEROMETER

[75] Inventor: John P. Rahn, Ridgecrest, Calif.

[73] Assignee: The United States of America as represented by the Secretary of the Navy, Washington, D.C.

[21] Appl. No.: 49,693

[22] Filed: Jun. 18, 1979

[51] Int. Cl.³ ..................... G01N 21/01; G02B 27/14
[52] U.S. Cl. ............................. 356/445; 350/276 SL; 356/342
[58] Field of Search ......................... 356/445, 446–448, 356/337, 338, 342, 256, 350; 350/276 SL

[56] References Cited

U.S. PATENT DOCUMENTS

| | | | |
|---|---|---|---|
| 2,451,501 | 10/1948 | Liben .................................. | 356/448 |
| 2,604,809 | 7/1952 | Mitchell .................................. | 88/14 |
| 3,621,220 | 11/1971 | Ford, Jr. .................................. | 235/181 |
| 3,734,626 | 5/1973 | Roberts et al. ...................... | 356/120 |
| 3,864,043 | 2/1975 | Russell .................................. | 356/152 |
| 3,952,583 | 4/1976 | Rosati .................................. | 73/71.3 |
| 3,977,789 | 8/1976 | Hunter et al. ........................ | 356/120 |
| 3,992,103 | 11/1976 | Tyley et al. .......................... | 356/335 |
| 3,998,552 | 12/1976 | Stewart et al. ...................... | 356/337 |
| 4,017,186 | 4/1977 | Shofner et al. ...................... | 356/337 |

OTHER PUBLICATIONS

Leinert, C. et al., "Stray Light Suppression in Optical Space Experiments", Applied Optics, vol. 13, No. 3, Mar. 1974, pp. 556-564.

Balth van der Pol, "The Nonlinear Theory of Electric Oscillations", IRE, vol. 22, No. 9, p. 1051 (1934).

Adler, "A Study of Locking Phenomena in Oscillators", IRE, vol. 34, p. 351 (1946).

Aronowitz et al., "Positive Scale Factor Correction in the Laser Gyro", IEEE, vol. QE13, No. 5, p. 338 (1977).

*Primary Examiner*—John K. Corbin
*Assistant Examiner*—Bruce Y. Arnold
*Attorney, Agent, or Firm*—R. S. Sciascia; W. Thom Skeer; Kenneth G. Pritchard

[57] ABSTRACT

Stray scattering in a scatterometer is removed by use of a lens and aperture system in conjunction with a beamsplitter. Backscattered light from a mirror being tested is deflected by a beamsplitter and focused by a lens through an aperture onto a detector. The distance from the beamsplitter to the lens is much smaller than the distance from the mirror to the beamsplitter in order to increase the detected signal as compared with detected noise caused by light scattered by the beamsplitter. The scatterometer system disclosed is further refined by use of a cavity dumper which absorbs stray light left after reflection from the mirror being tested. The cavity dumper is a silicon semiconductor on a metal backing which absorbs the light with minimum reflection back along the original incident light path.

15 Claims, 3 Drawing Figures

STRAY LIGHT ELIMINATOR IN A SCATTEROMETER

BACKGROUND OF THE INVENTION

1. Field of the Invention

This invention relates to scatterometer systems and in particular to scatterometer systems which eliminate stray light. Further this system relates to scatterometers which in addition to having stray light eliminated are able to dump excess light without heating or other surplus light problems.

2. Description of the Prior Art

Previous systems used for scattering measurements from mirrors had no way of controlling back scattered light from entering the light emission source. The use of retroscatter in a device such as a laser gyro causes a problem of lock-in between the output wave from a laser and the reflected wave back along that path. When the waves lock together in frequency, no rotational information for a laser gyro can be obtained. The lock-in phenomena becomes a serious problem when two oscillators with only slight separation of operating frequencies couple together. In this case, there is a weak coupling mechanism which will cause both of them to oscillate at the same frequency. An example of this is the known fact that when two mechanical clocks have nearly the same frequency, they become weakly coupled acousticly by the sound each makes. The article "The Nonlinear Theory of Electric Oscillations" by Balth van der Pol in Proceedings of the Institute of Radio Engineers, Vol. 22, No. 9, September 1934, first analysed the lock-in phenomena as an effect in triode oscillators. A simplification of this analysis has since been published by Robert Adler in an article titled "A Study of Locking Phenomena in Oscillators" in the "Proceedings of the IRE and Waves in Electrons", Vol. 34, June 1946, page 351.

In the laser gyro, two oscillators are nominally independent with two counter propagating waves. These are weakly coupled by the light of one wave which retroscatters from the mirror and combines at a different phase and frequency with the light of the other counter propagating wave. When the frequencies of the two waves are sufficiently separated, which occurs when the laser gyro is rotating rapidly, the waves will not lock together. A recent paper on this laser gyro lock-in phenomena is "A Positive Scale Factor Correction in the Laser Gyro" by Fred Aronowitz and Wah L. Lim in the "IEEE Journal of Quantum Electronics," Vol. QE-13, No. 5, page 338, May 1977. At low gyro rotation rates, which imply small frequency separations, the waves lock together and no information about rotation rate can be obtained. There are two ways in which one can combat this lock-in phenomena. One is to apply a small mechanical oscillation motion called dither. This helps, but leads to a certain amount of undesirable random drift in the output. The second way to combat the lock-in is to develop lower scatter laser mirrors. To do this, more effective methods of measuring retroscatter are needed.

SUMMARY OF THE INVENTION

Light from a source, such as a laser, is incident on a beamsplitter at a relatively large incident angle. Half of the light will be deflected by the beamsplitter into a side direction while the other half of the light passes through the beamsplitter. The light then strikes a mirror which is being measured within the scatterometer. While most of this light will be reflected away and require a cavity dumper to keep it from causing any unwanted scatter, part of the light striking any mirror at any orientation will be retroscattered directly back along the incident path to the beamsplitter. This light, which goes back into the light source, would cause a lock-in problem if the mirror is used in a laser gyro. When this light strikes the beamsplitter, it is deflected in a direction approximately 90° to the incident direction. This light is focused by a lens to a predetermined spot and passed through an apertured screen. As it passes through the apertured screen, it is incident on a photodetector which measures the light present. It has been shown that direct retroscatter measurement yields a result about equal to that of near retroscatter. Near retroscatter means that scatter is being measured within about 2° of retroscatter direction for the instrument.

DESCRIPTION OF THE PREFERRED EMBODIMENT

Figure 1:
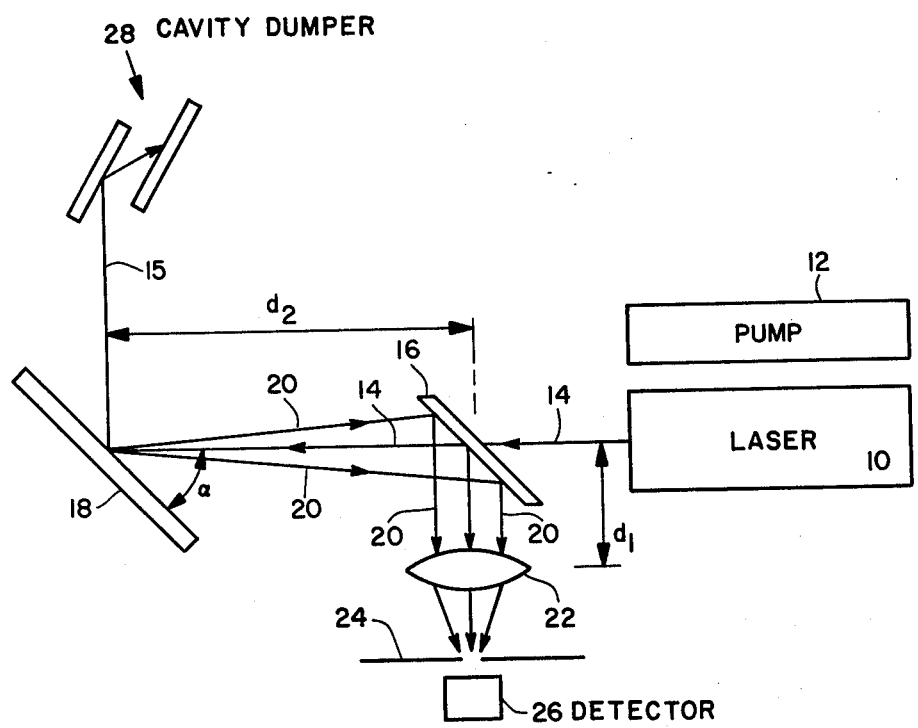
FIG. 1 is a diagram of the present invention.

In FIG. 1, a system for eliminating stray light from a scatterometer is shown. A light source emits a light beam such as a laser. A laser source is shown comprised of any suitable laser material 10. Laser material 10 is stimulated to light emission by pumping means 12. Laser material 10 emits light beam 14 which passes through a beamsplitter 16 and continues on to a mirror 18. Mirror 18 is being tested for its reflectivity. Mirror 18 is oriented at some arbitrary angle $\alpha$ to incident light 14 such that light 14 is reflected off into a new predetermined direction 15. However, despite the orientation of mirror 18, some light will be retroscattered back toward beamsplitter 16. This light is represented by arrows 20. Light 20 can cause a lock in phenomena when used with a laser source such as a laser gyro. To evaluate the quality of the surface of mirror 18, the amount of retroscatter must be determined. This is done in FIG. 1 by use of a lens 22 which is positioned to focus light 20 after it has been reflected off of beamsplitter 16 as shown. Lens 22 converges light 20 to a predetermined spot which is shown through an apertured screen 24. The light is then measured by a detector 26. Since the bulk of light 14 will not retroscatter from mirror 18, a cavity dumper 28 is used to absorb the unwanted light and prevent it from causing heating or other problems.

In the above figure, which is not drawn to scale, it is important to consider the relation of aperture size to distance to the sample mirror. A controlling relationship of distances is found in the thin lens equation:

$$(1/I) + (1/0) = (1/f)$$

where I is the distance of the image from the lens, 0 is the distance of the object, the light spot on the sample mirror, from the lens and f is the focal length of the telescope. As is well-known, solving for I yields $I = (0f/0 - f)$. The aperture size itself, $d_a$, is dependent on d, the diameter of the illuminated spot on the mirror, and the ratio of (I/0). In general, the requirement for the aperture size is that $d_a$ is greater than or equal to $d(I/0)$ which can be expressed as:

$$d_a \geq d\left(\frac{f}{0-f}\right)$$

To eliminate interference from the beamsplitter, it is important to have the distance from the beamsplitter, to the lens much smaller than the distance from the beamsplitter to the sample. As shown in FIG. 1, the distance from the beamsplitter to the lens is referred to as $d_1$ and the distance from the beamsplitter to the sample is shown as $d_2$. An alternate way of thinking of the above requirements is that if the quantity $a_s$ represents the area of the laser beam spot on the sample mirror 18 and $a_L$ represents the illuminated area of lens 22 then the ratio of power from the sample reaching the detector to that from the beamsplitter is:

$$(p_s/p_b) = (a_L/a_s)$$

where $p_s$ represents the power from the sample and $p_b$ represents the power from the beamsplitter. This equation assumes equal scatter in the direction of the detector from the mirror and from the beamsplitter. Detector 26 shown in FIG. 1 is ideally thought of as a small semiconductor detector. The phrase small detector is representative of using a semiconductor detector with low capacitance and high resistance. High capacitance and low resistance found in detectors of larger area result in coupling of the normal voltage flicker at the input of a preamplifier to the output of the detector, thus increasing the noise of the output. In the visible and near infrared, this preamp noise limits sensitivity more than detector noise. For this reason, photomultipliers will usually be used in the visible light region in order to get essentially noise free multipication of photoelectrons generated.

Units of measurement in the present invention are characterized by the symbol F which represents the fractional scatter per steradian, which is the unit needed to insert into a lock-in equation. A Lambertian scatter calibration is used:

$$F = (v_m r / v_L \pi)$$

where $v_m$ is the detector voltage from the mirror, $v_L$ is the detector voltage measured if the Lambertian scatterer is viewed along the normal of the sample, r is the known diffuse reflectance of the Lambertian scatterer and $\pi$ is 3.1416. The quantity, $v_m$, the detector voltage from the mirror, is measured in spherical coordinates from the normal to the sample mirror.

Figure 2:
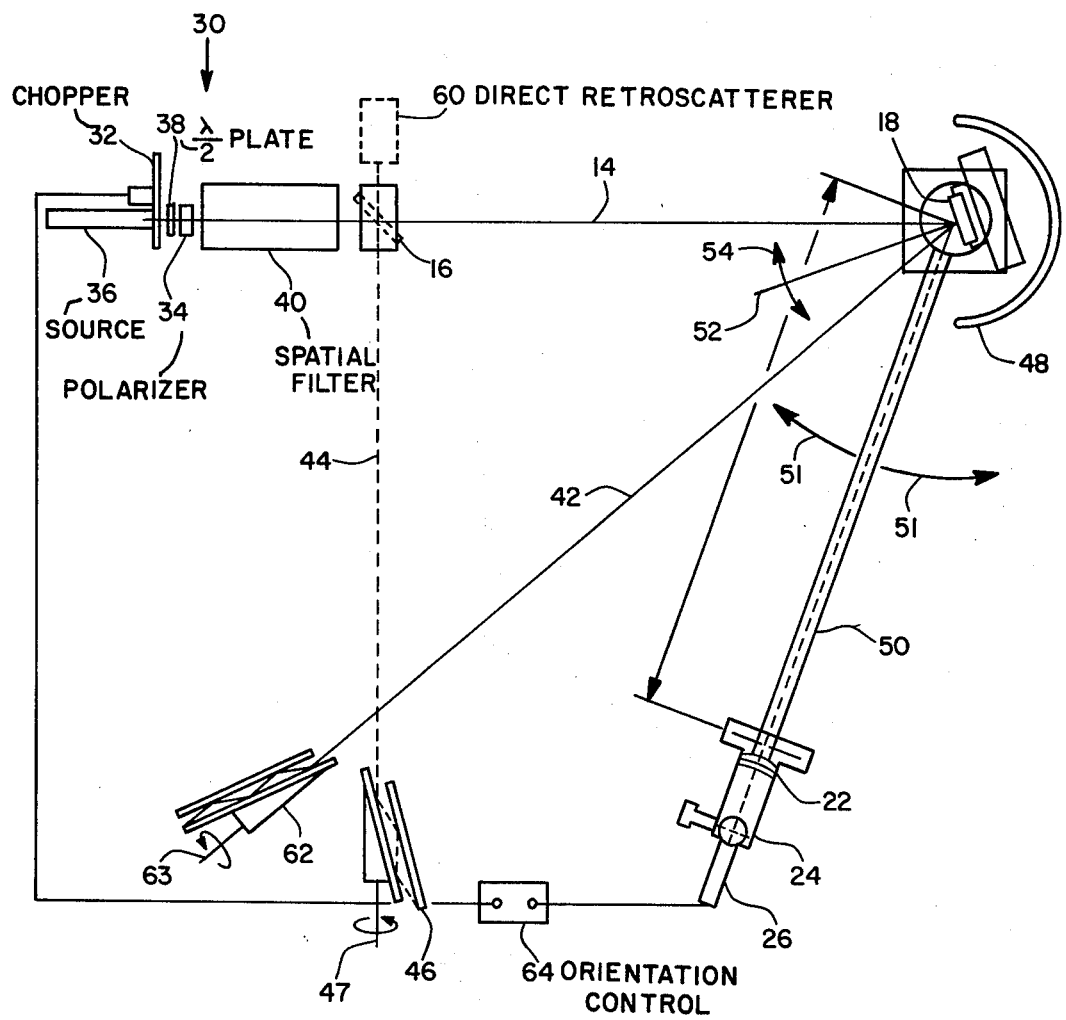
FIG. 2 is a diagram of an alternate embodiment of the present invention.

FIG. 2 shows an alternate embodiment of the present invention which allows for controlled stepping of the sample mirror through different incident angles. It is comprised of a light source 30 which includes a light chopper 32 and a filter or polarizer 34. Actual light is provided from a source 36 which is chopped and filtered through a rotatable halfwave length plate 38 and then polarized by polarizer 34. A cross-sectional plot across the beam after leaving polarizer 34 shows a Gaussian distribution of power per unit area except for a background noise level in the wings of the Gaussian curve. The beam is then "cleaned up" by a very carefully chosen spatial filter 40 so that it emerges from this device as a perfect Gaussian light beam. Spatial filter 40 can be a well defined aperture that blocks the light in the wings from propagating. The cross-section is now a Gaussian curve with the wings removed, however, for experimental purposes the beam behaves as a perfect Gaussian distribution. A good usable beam has been used having a 1 mm ($1/e^2$) diameter where e is the natural log base. The light is collimated at this point also. Light incident on beamsplitter 16 will have a component reflected in the direction of the dotted line 44 and a component which passes through the beamsplitter along arrow 14. Lost light 44 is absorbed by a cavity dumper 46. Sample mirror 18 is now stepped through controlled rotation steppers represented by an incident angle adjust mechanism 48. Incident angle adjust mechanism 48 is in turn subject to being pivoted about rotating telescope boom 50. However, incident angle adjust mechanism 48 can also be located on the end of telescope boom 50 and still have the boom rotate throughout the plane of incidence. This permits sample mirror 18 to step through an angular range about the mirror normal 52 as shown by arrow 54. Telescope boom 50 has the same arrangement of lens 22, apertured screen 24 and detector 26 shown in FIG. 1. Telescope boom 50 can measure all light scattered in random directions from main reflected light 42. To measure near retroscatter, telescope boom 52 is placed within a few degrees of light 14. The direct retroscatter measurement mechanism previously discussed as shown in FIG. 1 is contained in the general box 60. If beamsplitter 16 is 50% reflective, the measurement will be half of the direct retroscatter from mirror 18. Reflected light from the sample mirror is absorbed by beam dumper 62 as shown. Both beam dumpers 46 and 62 are pivotably mounted so that they can maintain an effective absorption angle by being rotated around axis 47 or 63 if the polarization of the incident light on the mirror is changed. To be effective, light incident on the dumpers must be "P" polarized. Control electronics 64 maintains the proper relationship of cavity dumper orientation for the appropriate incident polarization angle.

Figure 3:
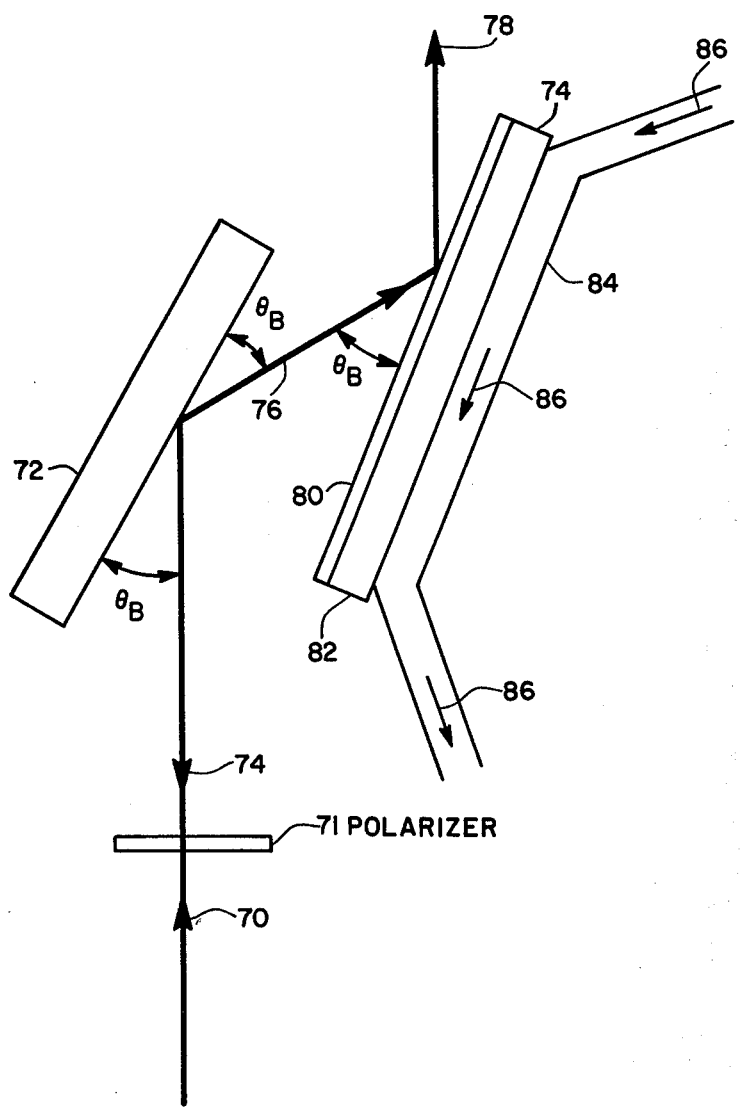
FIG. 3 is a diagram of a cavity dumper that can be used with the present invention.

FIG. 3 is a close-up diagram of a low scatter beam dumper suitable for the present invention. Light reflected from sample mirror 18, not shown in FIG. 3, is shown traveling in the direction of arrow 70. This light is incident on a slab 72 at a relatively high incident angle. Some light will be retroscattered along the original path indicated by arrow 74. This light could continue back into the light source system. For a laser circuit, this can damage the laser circuit and interfere with measurements that are made along the incident beam such as those shown in FIG. 1. For the light shown in FIG. 3, maximum absorption can be obtained by use of P polarized light. Light 70 can be polarized by a filter 71 inserted between the sample mirror 18 and slab 72 or it can be polarized prior to its use in the system as shown in FIG. 2. Slab 72 is a polished semiconductor. A semiconductor can be any material that has a conduction valence band gap less than the energy of the incident photos contained in beam 70. For maximum efficiency, the incident angle shown should be near the Brewster angle. If slab 72 is a silicon semiconductor, the angle is 74.5°. The significance of the Brewster angle is that it has a very low retroscatter coefficient. Thus the proper matching of band gap and Brewster angle in combination, permit a high percentage of the light to be absorbed rather than reflected. In addition, what light is reflected is very highly reflected in the forward direction as shown by arrow 76. To provide close to total absorption, beam 76 is set to impinge on a second slab 74. Should further absorption be necessary, another slab for beam 78 can be provided.

It is also possible, as shown in FIG. 2, to orient these two slabs such that multiple reflections between them occur to provide the level of absorption necessary. Also it should be noted that if the surface of the semiconductor slab is highly polished, illumination at a high incident angle, such as the Brewster angle, improves the tendency to approach zero backscatter. It can be shown mathematically that this property will tend toward zero as an inverse function of the wavelength, roughness correlation length, and the size of the incident angle as measured from the normal to the surface.

A further refinement for a cavity dumper is shown for slab 74. Slap 74 consists of a semiconductor film 80 which is deposited on a metal backing 82. The film can be made with a high degree of smoothness and the absorption of energy in film 80 will be readily passed onto metal backing 82. Metal backing 82 can now be cooled through a heat sink 84 which can take the form of a cooling fluid traveling in a channel as shown by arrows 86. The cooling fluid 86 can thus pass into any well-known heat exchanger and maintain metal backing 82 at any desired temperature. The obvious advantage of this situation is that no localized heat buildup will occur in film 80 which could cause breakdown of the semiconductor absorbing film.

What is claimed is:

1. A stray light eliminator in a scatterometer comprising:
   a light source for emitting a light beam;
   a beamsplitter of predetermined reflectivity placed in the path of said emitted light beam for scattering a predetermined amount of light in a direction different from said emitted light path;
   a mirror placed in the path of said emitted light that has passed through said beamsplitter without being scattered for reflecting said light in a predetermined direction other than back along said emitted light path, said mirror having an inherent tendency to retroscatter some light back along said emitted path and into said light source after passing back through said beamsplitter where part of said retroscattered light is reflected in a direction unique to said retroscattered light;
   a lens placed in the path of said retroscattered light which has been reflected by the beamsplitter for converging said retroscattered light to a predetermined spot, the distance from the beamsplitter to the lens being much smaller than the distance from said mirror to the beamsplitter to increase the detected signal retroscattered from said mirror as compared with the detected noise caused by light scattered from said beamsplitter;
   an apertured screen placed in the path of said converged light for limiting light behind said screen to only said converged light which passes through said aperture;
   a detector placed behind said screen for measuring the level of light passing through said aperture; and
   a beam dumper placed in the path of reflected light from said mirror for absorbing unwanted light.

2. A stray light eliminator in a scatterometer as described in claim 1 wherein said light source comprises a laser material in proximity to a pump source which stimulates said material such that coherent light is emitted.

3. A stray light eliminator in a scatterometer as described in claim 1 wherein said detector comprises a semiconductor detector.

4. A stray light eliminator in a scatterometer as described in claim 3 wherein said semiconductor detector comprises a silicon detector with low capacitance and high resistance.

5. A stray light eliminator in a scatterometer as described in either of claims 3 or 4 wherein said light source comprises a laser material in proximity to a pump source which stimulates said material such that coherent light is emitted.

6. A stray light eliminator in a scatterometer as described in claim 1 wherein said beam dumper comprises a plurality of slabs of semiconductor material with a conduction to valence band gap less than the energy of the incident photons in said light beam such that said semiconductor slabs absorb said incident light.

7. A stray light eliminator in a scatterometer as described in claim 6 wherein said semiconductor slabs are comprised of silicon and positioned to intersect said incident light to be absorbed at the Brewster angle.

8. A stray light eliminator as described in either claim 6 or claim 7 wherein said light source comprises a laser material in proximity to a pump source which stimulates said material such that coherent light is emitted.

9. A stray light eliminator as described in any of claims 1, 2, 3, 4, 6 or 7 wherein said beamsplitter has a reflectivity of 50%.

10. A stray light eliminator in a scatterometer comprising:
    a laser material for emitting light along an optical path;
    a pump source in proximity to said laser material for stimulating said emitted light;
    a beamsplitter with 50% reflectivity placed in the path of said emitted light for scattering a predetermined amount of light in a direction different from said optical path;
    a mirror placed in the path of said emitted light that has passed through said beamsplitter without being scattered for reflecting said light in a different predetermined direction other than back along said emitted light path, said mirror having an inherent tendency to retroscatter some light back along said emitted path and into said laser material after passing back through said beamsplitter;
    a lens placed in the path of light scattered in said different direction by said beamsplitter for converging said scattered light to a predetermined spot;
    an apertured screen placed in the path of said converged light for limiting light behind said screen to only said converged light which passes through said aperture;
    a silicon photodetector with low capacitance and high resistance placed behind said screen for measuring the level of light passing through said aperture;
    a beam dumper placed in the path of reflected light from said mirror for absorbing unwanted light, said beam dumper comprised of silicon film deposited on a metal backing, said silicon film having a conduction to valence band gap less than the energy of the incident photons in said reflected light beam; and
    a heat sink connected to said metal backing for preventing heat buildup in said silicon film.

11. A stray light eliminator in a scatterometer comprising:

laser material for emitting light along an optical path;

a pump source in proximity to said laser material for stimulating said emitted light;

a polarizer in said optical path for P polarizing said emitted light beam;

a spatial filter in said optical path for adjusting said polarized emitted light to be a Gaussian light beam;

a mirror placed in the path of said Gaussian light beam for reflecting said Gaussian light beam in a different predetermined direction other than back along said optical path said mirror having an inherent tendency to retroscatter some light back along said optical path and into said laser material;

an incident angle adjust mechanism holding said mirror for stepping said mirror through a predetermined range of incident angles to said Gaussian light beam;

a rotating telescope boom pivoted on said incident angle adjust mechanism for looking at light scatter in any arbitrary direction for any step of said incident angle adjust mechanism;

a lens within said rotating telescope boom for converging said scattered light to a predetermined spot;

an apertured screen placed in the path of said converged light for limiting light behind said screen to only said converged light which passes through said aperture;

a detector placed behind said screen for measuring the level of light passing through said aperture; and a beam dumper placed in the path of reflected light from said mirror for absorbing unwanted light.

12. A stray light eliminator in a scatterometer as described in claim 11 wherein said detector comprises a semiconductor detector.

13. A stray light eliminator in a scatterometer as described in claim 12 wherein said semiconductor detector comprises a silicon detector with low capacitance and high resistance.

14. A stray light eliminator in a scatterometer as described in claim 11 wherein said beam dumper comprises a plurality of slabs of semiconductor material with a conduction to valence band gap less than the energy of the incident photons in said light beam such that said semiconductor slabs absorb said incident light.

15. A stray light eliminator in a scatterometer as described in claim 14 wherein said semiconductor slabs are comprised of silicon and positioned to intersect said incident light to be absorbed at the Brewster angle.

* * * * *